US007939511B2

(12) United States Patent
Doi et al.

(10) Patent No.: US 7,939,511 B2
(45) Date of Patent: May 10, 2011

(54) OPHTHALMIC COMPOSITION CONTAINING XANTHAN GUM AND AMINO ACID

(75) Inventors: Koji Doi, Kobe (JP); Hiroshi Aki, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 170 days.

(21) Appl. No.: 11/663,771

(22) PCT Filed: Sep. 27, 2005

(86) PCT No.: PCT/JP2005/018239
§ 371 (c)(1),
(2), (4) Date: Apr. 11, 2007

(87) PCT Pub. No.: WO2006/035969
PCT Pub. Date: Apr. 6, 2006

(65) Prior Publication Data
US 2008/0039423 A1 Feb. 14, 2008

(30) Foreign Application Priority Data

Sep. 28, 2004 (JP) ................. 2004-281588

(51) Int. Cl.
*A61K 31/723* (2006.01)
*A61K 31/198* (2006.01)
(52) U.S. Cl. .......................... 514/54; 514/561
(58) Field of Classification Search ............... 514/54, 514/561
See application file for complete search history.

(56) References Cited

U.S. PATENT DOCUMENTS

| 4,136,177 | A | 1/1979 | Lin et al. |
| 5,013,714 | A | 5/1991 | Lindstrom et al. |
| 5,571,503 | A | 11/1996 | Mausner |
| 5,846,950 | A | 12/1998 | Fedorov et al. |
| 2002/0035088 | A1 | 3/2002 | Perdiguer et al. |
| 2003/0068250 | A1* | 4/2003 | Huth et al. ............... 422/25 |
| 2004/0034042 | A1* | 2/2004 | Tsuji et al. ............ 514/263.31 |
| 2005/0136391 | A1* | 6/2005 | Steinhardt ............... 435/1.1 |

FOREIGN PATENT DOCUMENTS

| CN | 1085081 | 1/1994 |
| EP | 0 136 782 | 4/1985 |
| EP | 0 778 021 | 6/1997 |
| EP | 0 799 615 | 10/1997 |
| EP | 1358883 A1 * | 11/2003 |
| JP | 06-25005 | 2/1994 |
| JP | 08-291060 | 11/1996 |
| JP | 10-109934 | 4/1998 |
| JP | 11-279194 | 10/1999 |
| JP | 2001-508035 | 6/2001 |
| JP | 2001-253822 | 9/2001 |
| JP | 2001-516713 | 10/2001 |
| JP | 2002-20279 | 1/2002 |
| JP | 2002-501017 | 1/2002 |
| JP | 2002-501533 | 1/2002 |
| JP | 2002-506461 | 2/2002 |
| JP | 2002-510654 | 4/2002 |
| JP | 2002-521332 | 7/2002 |
| JP | 2002-521333 | 7/2002 |
| JP | 2003-128553 | 5/2003 |
| JP | 2003-137781 | 5/2003 |
| JP | 2004-59432 | 2/2004 |
| JP | 2004-203836 | 7/2004 |
| JP | 2005-53905 | 3/2005 |
| JP | 2005-60279 | 3/2005 |
| RU | 2 056 821 | 3/1996 |
| RU | 2 198 633 | 2/2003 |
| WO | 93/23017 | 11/1993 |
| WO | 98/17249 | 4/1998 |
| WO | 98/53809 | 12/1998 |
| WO | 99/00133 | 1/1999 |
| WO | 99/13863 | 3/1999 |
| WO | 99/37292 | 7/1999 |
| WO | 99/51273 | 10/1999 |
| WO | 00/04899 | 2/2000 |
| WO | WO 0249611 A2 * | 6/2002 |
| WO | 03/092706 | 11/2003 |

OTHER PUBLICATIONS

Santvliet et al. Eur. J. Pharm. Sci., 1999, 7, p. 339-345.*
English machine translation of Japanese Patent Document JP 2004-203836, http://dossier1.ipdl.inpit.go.jp/, accessed online on Jun. 14, 2010.*
Letter dated Jun. 29, 2009 from China Science Patent and Trademark Agent LTD. showing receipt of Office Action issued Jun. 5, 2009 from the Chinese Patent Office with translation of text portion of the Office Action.
L. Romanelli et al., "Ocular Absorption and Distribution of Bendazac After Topical Administration to Rabbits with Different Vehicles", Life Sciences, vol. 54, No. 13, Jan. 1, 1994, pp. 877-885.
Database WPI Week 200239 Thompson Scientific, AN 2002-355876, XP 002553727, Abstract to JP 2002-20279.
Database WPI Week 199703 Thompson Scientific, AN 1997-029454, XP 002553728, Abstract to JP 08-291060.
Database WPI Week 199651 Thompson Scientific, AN 1996-516743, XP 002553729, Abstract to RU 2056821.
Database WPI Week 199412 Thompson Scientific, AN 1994-094801, XP 002553730, Abstract to JP 06-025005.
Database WPI Week 200369 Thompson Scientific, AN 2003-729221, XP 002553731, Abstract to RU 2 198 633.
Database WPI Week 200367 Thompson Scientific, AN 2003-700800, XP 002553732, Abstract to JP 2003-128553.

(Continued)

*Primary Examiner* — Shaojia Anna Jiang
*Assistant Examiner* — Jonathan S Lau
(74) *Attorney, Agent, or Firm* — Wenderoth, Lind & Ponack, L.L.P.

(57) ABSTRACT

The present invention provides an ophthalmic composition containing xanthan gum, or xanthan gum and an amino acid, which has a superior corneal epithelial disorder-treating effect and a superior corneal epithelial cell-protecting effect.

2 Claims, No Drawings

OTHER PUBLICATIONS

Database WPI Week 199954 Thompson Scientific, AN 1999-629280, XP 002553733, Abstract to JP 11-279194.

Database WPI Week 200203 Thompson Scientific, AN 2002-021021, XP 002553734, Abstract to JP 2001-253822.

European Patent Office Office Action issued Jan. 19, 2011 in corresponding European Application No. 05 788 319.1, in the English language.

* cited by examiner

OPHTHALMIC COMPOSITION CONTAINING XANTHAN GUM AND AMINO ACID

This application is a U.S. national stage of International Application No. PCT/JP2005/018239 filed Sep. 27, 2005.

TECHNICAL FIELD

The present invention relates to an ophthalmic composition containing xanthan gum, or xanthan gum and an amino acid, which is used for the treatment of a corneal epithelial disorder.

BACKGROUND ART

Lacrimal fluid covers eye ball surface consisting of cornea and conjunctiva to maintain wettability of cornea and conjunctiva, and prevents drying. In recent years, however, an increasing number of people report various symptoms including feeling of fatigue and foreign sensation, namely, dry eye syndromes, which are caused by dry surface of cornea and conjunctiva due to lacrimal fluid decrease, dryness of eye during wearing contact lenses, or dryness of eye during operation of OA equipment and the like. Dry eye sometimes accompanies corneal epithelial disorder, corneal epithelial erosion and the like due to disorders of corneal epithelial cells. In a serious case, corneal ulceration and eye infection may be developed. To mitigate such various conditions caused by drying, artificial lacrimal fluids containing salts such as sodium chloride and the like as a main ingredient, eye drops containing hydroxyethylcellulose, chondroitin sulfate or hyaluronic acid and the like have been used. As the situation stands, however, there is no satisfactory agent as yet.

Lacrimal fluid is said to show pseudoplasticity. That is, the viscosity of lacrimal fluid decreases when a force is applied by blinking, and increases when the force is not applied. Therefore, lacrimal fluid has unique property in that it has low viscosity and becomes thin during blinking to facilitate blinking, but it becomes highly viscose before and after blinking to cover the eye surface for protection. As a polymer compound showing such pseudoplasticity, xanthan gum is known.

As an ophthalmic composition containing xanthan gum, the following have been reported. For example, an ophthalmic composition containing echothiopate iodide and xanthan gum is disclosed, and xanthan gum has been reported to enhance the treatment effect of echothiopate iodide (U.S. Pat. No. 4,136,177). In addition, an ophthalmic composition containing xanthan gum and a carbonate dehydratase inhibitor has been disclosed, where xanthan gum is used to improve ophthalmic bioavailability of the carbonate dehydratase inhibitor (JP-T-2001-508035, JP-T-2002-501017, JP-T-2002-506461). For the purpose of improving ophthalmic bioavailability of a drug, xanthan gum is used, and an ophthalmic composition containing a carbonate dehydratase inhibitor, a prostaglandin derivative and xanthan gum has been disclosed (JP-T-2002-501533, JP-T-2002-521332, JP-T-2002-521333). An ophthalmic composition containing quaternary nitrogen-containing ethoxylated glycoside and xanthan gum has been disclosed for the treatment of dry eye (JP-T-2001-516713). In addition, an ophthalmic composition containing xanthan gum, which is gelated upon contact with the eye, has been disclosed (JP-T-2002-510654).

However, no report is found on an ophthalmic composition containing xanthan gum and an amino acid. Moreover, it is not known that xanthan gum has a corneal epithelial cell protecting action, or corneal epithelial cell protecting action can be improved by combining xanthan gum and an amino acid.

DISCLOSURE OF THE INVENTION

An object of the present invention is to provide an ophthalmic composition having good usability and a superior treatment effect for corneal epithelial disorders. Specifically, the object is to provide an ophthalmic composition having a superior corneal epithelial cell protecting effect.

The present inventors have conducted intensive studies in an attempt to achieve the above-mentioned object and found that xanthan gum has a corneal epithelial cell protecting action in a culture test system of corneal epithelial cells, and a cell protecting action can be improved by combining xanthan gum and an amino acid, based on which finding they have proceeded further with the studies and completed the present invention.

Accordingly, the present invention can provide the following.

(1) An ophthalmic composition comprising xanthan gum.
(2) The ophthalmic composition of 1, further comprising an amino acid.
(3) The ophthalmic composition of 2, wherein the amino acid is at least one selected from aspartic acid, aminoethyl sulfonic acid, chondroitin sulfate and a pharmacologically acceptable salt thereof.
(4) The ophthalmic composition of any one of 1 to 3, wherein the concentration of the xanthan gum therein is 0.05-0.4 w/v %.
(5) The ophthalmic composition of any one of 2 to 4, wherein the concentration of the amino acid therein is 0.05-2 w/v %.
(6) The ophthalmic composition of any one of 1 to 5, which is used for the treatment of a corneal epithelial disorder.
(7) The ophthalmic composition of 6, wherein the corneal epithelial disorder is a disorder in a corneal epithelial cell.
(8) The ophthalmic composition of any one of 1 to 5, which is used for protecting a corneal epithelial cell.
(9) The ophthalmic composition of any one of 1 to 8, which is an eye drop.
(10) Use of xanthan gum for the production of a pharmaceutical agent for the treatment of a corneal epithelial disorder.
(11) Use of xanthan gum for the production of a pharmaceutical agent for protecting a corneal epithelial cell.
(12) Use of xanthan gum and an amino acid for the production of a pharmaceutical agent for the treatment of a corneal epithelial disorder.
(13) Use of xanthan gum and an amino acid for the production of a pharmaceutical agent for protecting a corneal epithelial cell.
(14) Use of 12 or 13, wherein the amino acid is at least one selected from aspartic acid, aminoethyl sulfonic acid, chondroitin sulfate and a pharmacologically acceptable salt thereof.
(15) The use of any one of 10 to 14, wherein the concentration of the xanthan gum therein is 0.05-0.4 w/v %.
(16) The use of any one of 12 to 15, wherein the concentration of the amino acid therein is 0.05-2 w/v %.
(17) A method for treating a corneal epithelial disorder, which comprises a step of administering an effective amount of xanthan gum to a subject of administration in need of the treatment.
(18) A method of protecting a corneal epithelial cell, which comprises a step of administering an effective amount of xanthan gum to a subject of administration in need of the protection.

(19) A method of treating a corneal epithelial disorder, which comprises a step of administering an effective amount of xanthan gum and an amino acid to a subject of administration in need of the treatment.

(20) A method of protecting a corneal epithelial cell, which comprises a step of administering an effective amount of xanthan gum and an amino acid to a subject of administration in need of the protection.

(21) The method of 19 or 20, wherein the amino acid is at least one selected from aspartic acid, aminoethyl sulfonic acid, chondroitin sulfate and a pharmacologically acceptable salt thereof.

(22) The method of any one of 17 to 21, wherein the concentration of the xanthan gum therein is 0.05-0.4 w/v %.

(23) The method of any one of 19 to 22, wherein the concentration of the amino acid therein is 0.05-2 w/v %.

According to the present invention, an ophthalmic composition containing xanthan gum, or xanthan gum and an amino acid, having a superior effect of treating a corneal epithelial disorder can be provided.

Moreover, the ophthalmic composition of the present invention in the form of an eye drop has superior usability since it contains xanthan gum showing pseudoplasticity.

BEST MODE FOR EMBODYING THE INVENTION

The present invention is explained in more detail in the following.

The present invention provides an ophthalmic composition containing xanthan gum. In another embodiment, the ophthalmic composition containing xanthan gum of the present invention further contains an amino acid. In the following, these ophthalmic compositions are also collectively referred to as the ophthalmic composition of the present invention.

The ophthalmic composition of the present invention only needs to be a preparation that can be administered to a topical tissue of the eye and, for example, eye drops, plasters and pressure sensitive adhesives, ointments, lotions, cream and the like can be mentioned, preferably an eye drop. Moreover, the ophthalmic composition of the present invention can also be used as a contact lens solution.

Xanthan gum to be used for the ophthalmic composition of the present invention has an average molecular weight of generally 100000-50000000, preferably 200000-20000000, particularly preferably 1000000-10000000. As the xanthan gum, ECHO GUM series such as ECHO GUM T, ECHO GUM F and the like commercially available from DAINIPPON PHARMACEUTICAL CO., LTD., SAN-ACE series such as SAN-ACE NXG-S and the like commercially available from San-Ei Gen F.F.I. Inc., KELTROL series such as KELTROL CG, KELTROL CG-T and the like commercially available from Sansho Co., Ltd., and the like are used, with preference given to ECHO GUM T and KELTROL CG-T. The content of xanthan gum in the ophthalmic composition of the present invention is generally 0.005-1 w/v %, preferably 0.01-0.6 w/v %, more preferably 0.02-0.5 w/v %, particularly preferably 0.05-0.4 w/v %.

As the amino acids usable for the ophthalmic composition of the present invention, glycine, alanine, valine, leucine, isoleucine, phenylalanine, proline, serine, threonine, tyrosine, asparagine, glutamine, lysine, arginine, tryptophan, histidine, cysteine, methionine, aspartic acid, glutamic acid, aminoethyl sulfonic acid, chondroitin sulfate and a pharmacologically acceptable salt thereof can be mentioned. As the salt, sodium salt, potassium salt, calcium salt and magnesium salt can be mentioned. These are used in combination of one or more kinds. Amino acid that can be preferably used includes aspartic acid, aminoethyl sulfonic acid, chondroitin sulfate, glutamic acid, glycine, lysine and a pharmacologically acceptable salt thereof. Particularly preferably, aspartic acid, chondroitin sulfate, aminoethyl sulfonic acid or a pharmacologically acceptable salt thereof is used.

The content of the amino acid in the ophthalmic composition of the present invention is generally 0.01-10 w/v %, preferably 0.05-2 w/v %, more preferably 0.1-1 w/v %, particularly preferably 0.2-1 w/v %.

The ratio of the combination of xanthan gum and amino acid is generally within the range of 5:1-1:50, preferably within the range of 2:1-1:20, by weight ratio.

The ophthalmic composition of the present invention can contain various additives as appropriate, such as buffer, isotonicity agent, preservative, dissolution aids, stabilizer, chelating agent, thickener, pH adjusting agent and the like.

As the buffer, for example, boric acid or a salt thereof (sodium borate etc.), citric acid or a salt thereof (sodium citrate etc.), tartaric acid or a salt thereof (sodium tartrate etc.), gluconic acid or a salt thereof (sodium gluconate etc.), acetic acid or a salt thereof (sodium acetate etc.), phosphoric acid or a salt thereof (sodium hydrogenphosphate, sodium dihydrogenphosphate etc.), various amino acids such as glutamic acid, $\epsilon$-aminocaproic acid and the like and tris buffer etc., and a combination thereof can be mentioned.

As the isotonicity agent, for example, sorbitol, mannitol, glycerol, propylene glycol, sodium chloride, potassium chloride and the like can be mentioned.

As the preservative, for example, paraoxybenzoates, benzalkonium chloride, benzethonium chloride, benzyl alcohol, sorbic acid or a salt thereof, chlorhexidine gluconate, sodium dehydroacetate, cetylpyridinium chloride, alkyldiaminoethylglycine hydrochloride, chlorobutanol and the like can be mentioned.

As the dissolution aids, for example, polyvinylpyrrolidone, polyethylene glycol, propylene glycol, polyoxyethylene hydrogenated castor oil 60, polyoxy 40 stearate, polysorbate 80 (trade name: Tween 80) and the like can be mentioned.

As the stabilizer, for example, disodium edetate, thiosodium sulfate, ascorbic acid, cyclodextrin, condensed phosphoric acid or a salt thereof, sulfite, citric acid or a salt thereof, dibutylhydroxytoluene and the like can be mentioned.

As the chelating agent, for example, disodium edetate, sodium citrate, condensed phosphoric acid or a salt thereof (sodium condensed phosphate etc.) and the like can be mentioned.

As the thickener, for example, methylcellulose, hydroxyethylcellulose, hydroxypropylcellulose, hydroxypropylmethylcellulose, sodium carboxymethylcellulose, polyvinylpyrrolidone, polyvinyl alcohol, polyethylene glycol, hyaluronic acid and the like can be mentioned.

As the pH adjusting agent, for example, sodium hydroxide, potassium hydroxide, sodium carbonate, sodium hydrogencarbonate, boric acid or a salt thereof (sodium borate), hydrochloric acid, citric acid or a salt thereof (sodium citrate, sodium dihydrogen citrate etc.), phosphoric acid or a salt thereof (disodium hydrogen phosphate, potassium dihydrogen phosphate etc.), acetic acid or a salt thereof (sodium acetate, ammonium acetate etc.), tartaric acid or a salt thereof (sodium tartrate etc.) and the like can be mentioned.

The ophthalmic composition of the present invention is adjusted to have pH 3-10, preferably pH 5-8. The ophthalmic composition of the present invention has a corneal epithelial cell protecting action. Accordingly, the ophthalmic composition of the present invention is useful as an agent for the prophylaxis or treatment of a corneal epithelial disorder, particularly a corneal epithelial cell disorder associated with a corneal epithelial disorder.

In particular, the ophthalmic composition of the present invention is useful as an agent for the prophylaxis or treatment of corneal epithelial disorders caused by drying (e.g., lacrimal fluid decrease symptom, xerophthalmia, meibomian gland dysfunction, Sjogren's syndrome, keratoconjunctivitis sicca, blepharitis, Stevens-Johnson syndrome, dry eye syndrome such as dry eye and the like related to VDT (Visual Display Terminal) operations, corneal and conjunctival epithelial disorder caused by dry eye, corneal epithelial erosion, corneal ulceration, blepharitis, ocular pemphigus, vernal kerato-conjunctivitis, allergic conjunctivitis etc.), particularly as an agent for the prophylaxis or treatment of a corneal epithelial cell disorder associated with a corneal epithelial disorder caused by drying.

In addition, the ophthalmic composition of the present invention is useful as an agent for the prophylaxis or treatment of corneal epithelial disorders caused by ultraviolet rays (e.g., keratitis, snow blindness etc.), particularly as an agent for the prophylaxis or treatment of a corneal epithelial cell disorder associated with a corneal epithelial disorder caused by ultraviolet rays.

Moreover, the ophthalmic composition of the present invention is useful as an agent for the prophylaxis or treatment of corneal epithelial disorders caused by the contact with a preservative (e.g., keratitis punctata superficialis, corneal ulceration etc.), particularly as an agent for the prophylaxis or treatment of a corneal epithelial cell disorder associated with a corneal epithelial disorder caused by the contact with a preservative.

The ophthalmic composition of the present invention can also be used as an instillation composition for the prophylaxis or improvement of eye fatigue, dryness of eye, blurred vision, eye irritation, conjunctival injection, uncomfortableness by wearing contact lenses and the like.

The ophthalmic composition of the present invention can be used for the prophylaxis or treatment of the above-mentioned diseases or conditions in human and animals other than human [e.g., mammals other than human (domestic animals and pets such as swine, bovine, horse, dog and the like) etc.].

Accordingly, the present invention provides a method for the prophylaxis or treatment of the above-mentioned diseases or conditions, and the method comprises a step of administering an effective amount of xanthan gum or an effective amount of xanthan gum and an amino acid to a subject of administration in need of the treatment (e.g., human or animals other than human).

The present invention also provide a method of protecting a corneal epithelial cell and the method comprises a step of administering an effective amount of xanthan gum or an effective amount of xanthan gum and an amino acid to a subject of administration in need of the protection (e.g., human or animals other than human).

When xanthan gum and an amino acid are to be administered, a single preparation obtained by simultaneously preparing xanthan gum and an amino acid may be administered, or two kinds of preparations obtained by separately forming preparations of xanthan gum and amino acid may be simultaneously administered in combination, as long as xanthan gum and an amino acid can be combined at the time of administration.

While the dose of xanthan gum varies depending on the dosage form, and target disease, age, sex, body weight, condition and the like of the test subject, for example, the daily dose is generally within the range of 0.01 μg-10 μg preferably within the range of 0.02 μg-5 μg, for an adult (e.g., body weight 60 kg).

In addition, when amino acid is to be administered in combination with xanthan gum, while the dose of the amino acid varies depending on the dosage form, and target disease, age, sex, body weight, condition and the like of the test subject, for example, the daily dose is generally within the range of 0.01 μg-10 μg, preferably within the range of 0.02 μg-5 μg, for an adult (e.g., body weight 60 kg).

The combination ratio of xanthan gum and an amino acid whether they are to be administered as a single preparation or individual preparations, the weight ratio thereof is generally within the range of 5:1-1:50, preferably within the range of 2:1-1:20.

The daily dose of each component can be administered at once or in several portions. For example, when used as an eye drop, the ophthalmic composition of the present invention can be administered several times, preferably 1 to 6 times, a day by several drops, preferably 1 to 3 drops, per administration. The administration period is not particularly limited.

The present invention further provides a kit (commercial package) to be used for practicing the above-mentioned method. The kit contains the ophthalmic composition of the present invention, and further, a written matter stating that the composition can be used for the prophylaxis or treatment of the above-mentioned diseases or conditions, or that the composition can be used for the protection of corneal epithelial cell and the like (e.g., instruction sheet for practicing the above-mentioned method using the kit).

The present invention is explained in detail in the following by referring to Examples and Experimental Examples, which are not to be construed as limitative.

EXAMPLES

Experimental Example 1

Corneal Epithelial Cell Protecting Action by a Combination of Xanthan Gum and Aspartic Acid Against Disorder Due to Drying 1. Experimental Method This experiment was performed as described (Br. J. Opthalmol. 2001, 85, 610). A frozen normal rabbit corneal epithelial cell suspension (NRCE2, manufactured by Kurabo Industries Ltd.) was suspended in a culture medium (RCGM2, manufactured by Kurabo Industries Ltd.). This suspension was centrifuged (5 min, 400×g), and the supernatant was removed. The cells were suspended in 2 mL of a culture medium, 20 μL thereof was diluted with 20 μL of trypan blue, and viable cells were counted on a blood cell counting chamber. Then, the cells were inoculated to each well of a 96-well plate to $4\times10^3$ cells/well/μL, and cultured to confluence at 37° C., 5% $CO_2$ under moisturization (n=5). The culture supernatant was removed from the 96-well plate, 100 μL of phosphate buffer (pH7, test solution) or phosphate buffer (pH 7, control solution) containing various concentrations (w/v %) of potassium L-aspartate and/or xanthan gum (ECHO GUM T: trademark) was added, and the mixture was cultured at 37° C., 5% $CO_2$ under moisturization for 15 min. After culture, the added test solution or control solution was removed, and the cells were dried at room temperature for 30 min. A Cell Counting Kit-8 solution (100 μL, manufactured by DOJINDO LABORATORIES) was added to each well, and absorbance (wavelength 450 nm) was measured 2 hr later using a 96-well Microplate Reader (Labsystems Multiskan, trademark). The survival rate (%) of the corneal epithelial cell was determined using the following formula from the average value of absorbance of the test solution or control solution and the average value of absorbance of the non-treatment group.

$$\text{Survival rate (\%)} = \frac{\text{average value of absorbance of test solution or control solution addition group}}{\text{average value of absorbance of non-treatment group}} \times 100$$

2. Experimental Results

As shown in Table 1, the survival rate of the corneal epithelial cell treated with a 0.2%, 0.5% or 1% potassium L-aspartate solution containing 0.1% xanthan gum showed a higher value as compared to that of the cell treated with a potassium L-aspartate solution without xanthan gum. In addition, the survival rate when treated with a phosphate buffer containing 0.1% xanthan gum (xanthan gum alone solution) showed a higher value as compared to that of the cell treated with a mere phosphate buffer without xanthan gum. However, the survival rate improving effect by the addition of xanthan gum (difference in the survival rate between addition and non-addition of xanthan gum) was higher with the potassium L-aspartate solution than with the phosphate buffer.

TABLE 1

Survival rate improving effect by addition of xanthan gum to potassium L-aspartate solution

|  | survival rate (%) | | survival rate improving effect (B-A, %) |
| --- | --- | --- | --- |
|  | xanthan gum non-addition (A) | 0.1% xanthan gum addition (B) |  |
| 0.2% potassium L-aspartate solution | 84.4 | 98.6 | 14.2 |
| 0.5% potassium L-aspartate solution | 79.4 | 96.5 | 17.1 |
| 1% potassium L-aspartate solution | 72.9 | 89.9 | 17.0 |
| phosphate buffer | 71.4 | 79.7 | 8.3 |

As shown in Table 2, the survival rate of the corneal epithelial cell when treated with a 0.05% or 0.1% xanthan gum solution containing 1% potassium L-aspartate showed a higher value as compared to that of the cell treated with a xanthan gum solution without potassium L-aspartate. On the other hand, the survival rate when treated with a phosphate buffer containing 1% potassium L-aspartate (potassium L-aspartate alone solution) was almost the same as the value when treated with a mere phosphate buffer without xanthan gum. That is, the survival rate improving effect by the addition of potassium L-aspartate (difference in the survival rate between addition and non-addition of potassium L-aspartate) was higher with the xanthan gum solution than with the phosphate buffer.

These results indicate that a combination of xanthan gum and potassium L-aspartate improves a corneal epithelial cell protecting action.

TABLE 2

Survival rate improving effect by addition of potassium L-aspartate to xanthan gum solution

|  | survival rate (%) | | survival rate improving effect (B-A, %) |
| --- | --- | --- | --- |
|  | potassium L-aspartate non-addition (A) | 1% potassium L-aspartate addition (B) |  |
| 0.05% xanthan gum solution | 78.0 | 94.8 | 16.8 |
| 0.1% xanthan gum solution | 79.7 | 89.8 | 10.1 |
| phosphate buffer | 71.4 | 72.9 | 1.5 |

Experimental Example 2

Corneal Epithelial Cell Protecting Action by a Combination of Xanthan Gum and Aminoethyl Sulfonic Acid Against Disorder Caused by Drying 1. Experimental Method A similar operation as in Experimental Example 1 was performed using aminoethyl sulfonic acid instead of potassium L-aspartate.

2. Experimental Results

As shown in Table 3, the survival rate of the corneal epithelial cell when treated with a 0.1% xanthan gum solution containing 0.5% aminoethyl sulfonic acid showed a higher value as compared to that of the cell treated with a xanthan gum solution without aminoethyl sulfonic acid. In addition, the survival rate when treated with a phosphate buffer containing 0.5% aminoethyl sulfonic acid (aminoethyl sulfonic acid alone solution) showed a higher value as compared to that of the cell treated with a mere phosphate buffer without aminoethyl sulfonic acid. However, the survival rate improving effect by the addition of aminoethyl sulfonic acid (difference in the survival rate between addition and non-addition of aminoethyl sulfonic acid) was higher with the xanthan gum solution than with the phosphate buffer. The results indicate that a combination of xanthan gum and aminoethyl sulfonic acid improves a corneal epithelial cell protecting action.

TABLE 3

Survival rate improving effect by addition of aminoethyl sulfonic acid to xanthan gum solution

|  | survival rate (%) | | survival rate improving effect (B-A, %) |
| --- | --- | --- | --- |
|  | aminoethyl-sulfonic acid non-addition (A) | 0.5% aminoethyl-sulfonic acid addition (B) |  |
| 0.1% xanthan gum solution | 77.3 | 99.6 | 22.3 |
| phosphate buffer | 68.6 | 79.1 | 10.5 |

Experimental Example 3

Corneal Epithelial Cell Protecting Action by a Combination of Xanthan Gum and Sodium Chondroitin Sulfate Against Disorder Caused by Drying 1. Experimental Method A similar operation as in Experimental Example 1 was performed using sodium chondroitin sulfate instead of potassium L-aspartate.

2. Experimental Results

As shown in Table 4, the survival rate of the corneal epithelial cell when treated with a 0.1% xanthan gum solution containing 0.5% sodium chondroitin sulfate showed a higher value as compared to that when treated with a xanthan gum solution without sodium chondroitin sulfate. In addition, the survival rate when treated with a phosphate buffer containing 0.5% sodium chondroitin sulfate (sodium chondroitin sulfate alone solution) showed a higher value as compared to that when treated with a mere phosphate buffer without sodium chondroitin sulfate. However, the survival rate improving effect by the addition of sodium chondroitin sulfate (difference in the survival rate between addition and non-addition of sodium chondroitin sulfate) was higher with the xanthan gum solution than with the phosphate buffer.

The results indicate that a combination of xanthan gum and sodium chondroitin sulfate improves a corneal epithelial cell protecting action.

TABLE 4

Survival rate improving effect by addition of sodium chondroitin sulfate to xanthan gum solution

|  | survival rate (%) | | |
| --- | --- | --- | --- |
|  | sodium chondroitin sulfate non-addition (A) | 0.5% sodium chondroitin sulfate addition (B) | survival rate improving effect (B-A, %) |
| 0.1% xanthan gum solution | 81.4 | 92.0 | 10.6 |
| phosphate buffer | 71.1 | 77.4 | 6.3 |

Experimental Example 4

Corneal Epithelial Cell Protecting Action by a Combination of Xanthan Gum and Aspartic Acid Against Disorder Caused by Drying

1. Experimental Method

A similar operation as in Experimental Example 1 was performed except that the culture time at 37° C., 5% $CO_2$ was changed from 15 min to 5 min and drying condition was changed from room temperature for 30 min to 37° C. for 60 min.

2. Experimental Results

As shown in Table 5, the survival rate of the corneal epithelial cell when treated with a 0.2% potassium L-aspartate solution containing 0.4% xanthan gum showed a higher value as compared to that when treated with a potassium L-aspartate solution without xanthan gum. In addition, the survival rate when treated with a phosphate buffer containing 0.4% xanthan gum (xanthan gum alone solution) showed a higher value as compared to that when treated with a mere phosphate buffer without xanthan gum. However, the survival rate improving effect by the addition of xanthan gum (difference in the survival rate between addition and non-addition of xanthan gum) was higher with the potassium L-aspartate solution than with the phosphate buffer.

TABLE 5

Survival rate improving effect by addition of xanthan gum to potassium L-aspartate solution

|  | survival rate (%) | | survival rate improving effect (B-A, %) |
| --- | --- | --- | --- |
|  | xanthan gum non-addition (A) | 0.4% xanthan gum addition (B) |  |
| 0.2% potassium L-aspartate solution | 12.8 | 100 | 87.2 |
| phosphate buffer | 11.2 | 86.5 | 75.3 |

Experimental Example 5

Corneal Epithelial Cell Protecting Action of Xanthan Gum Against Disorder Caused by Preservative

1. Experimental Method

A frozen normal rabbit corneal epithelial cell suspension (NRCE2, manufactured by Kurabo Industries Ltd.) was suspended in a culture medium (RCGM2, manufactured by Kurabo Industries Ltd.). This suspension was centrifuged (5 min, 400×g), and the supernatant was removed. The cells were suspended in 2 mL of a culture medium, 20 µL thereof was diluted with 20 µL of trypan blue, and viable cells were counted on a blood cell counting chamber. Then, the cells were inoculated to each well of a 96-well plate to $4 \times 10^3$ cells/well/µL, and cultured to confluence at 37° C., 5% $CO_2$ under moisturization (n=6). The culture supernatant was removed from the 96-well plate, 100 µL of phosphate buffer (pH7) containing benzalkonium chloride, a phosphate buffer (pH7, test solution) or phosphate buffer (pH 7) containing xanthan gum (ECHO GUM T: trademark) or phosphate buffer (pH 7) was added, and the mixture was cultured at 37° C., 5% $CO_2$ under moisturization for 30 min. After culture, each added solution was removed, and the cells were washed twice with culture medium (100 µL). A Cell Counting Kit-8 solution (100 µL, manufactured by DOJINDO LABORATORIES) was added to each well, and absorbance (wavelength 450 nm) was measured 2 hr later using a 96-well Microplate Reader (Labsystems Multiskan, trademark). The survival rate (%) of the corneal epithelial cell was determined using the following formula from the average value of absorbance of each solution and the average value of absorbance of the non-treatment group.

$$\text{Survival rate (\%)} = \frac{\text{average value of absorbance of each test solution addition group}}{\text{average value of absorbance of non-treatment group}} \times 100$$

2. Experimental Results

As shown in Table 6, the survival rate when cultured with an aqueous solution containing a preservative, benzalkonium chloride, was lower than that by culture in the phosphate buffer. However, the survival rate was improved by further cultivation in an aqueous solution containing 0.1% or 0.4% xanthan gum.

The results indicate that xanthan gum has a corneal epithelial cell protecting action against a disorder caused by a preservative.

TABLE 6

Corneal epithelial cell protecting action of xanthan
gum against disorder caused by preservative

| solution | survival rate (%) of corneal epithelial cell |
|---|---|
| 0.0025% benzalkonium chloride + 0.1% xanthan gum aqueous solution | 49.3 |
| 0.0025% benzalkonium chloride + 0.4% xanthan gum aqueous solution | 100 |
| 0.0025% benzalkonium chloride aqueous solution | 37.7 |
| phosphate buffer | 92.9 |

Experimental Example 6

Corneal Epithelial Cell Protecting Action of Xanthan Gum Against Disorder Caused by Ultraviolet Rays 1. Experimental Method A frozen normal rabbit corneal epithelial cell suspension (NRCE2, manufactured by Kurabo Industries Ltd.) was suspended in a culture medium (RCGM2, manufactured by Kurabo Industries Ltd.). This suspension was centrifuged (5 min, 400×g), and the supernatant was removed. The suspension was centrifuged (5 min, 400×g), and the supernatant was removed. The cells were suspended in 2 mL of a culture medium, 20 μL thereof was diluted with 20 μL of trypan blue, and viable cells were counted on a blood cell counting chamber. Then, the cells were inoculated to each well of a 96-well plate to 4×10³ cells/well/μL, and cultured to confluence at 37° C., 5% $CO_2$ under moisturization (n=6). The culture supernatant was removed from the 96-well plate, 100 μL of phosphate buffer (pH 7) containing xanthan gum (ECHO GUM T: trademark) or phosphate buffer (pH 7) was added, and ultraviolet rays (about 20 μW/cm²) were irradiated for 90 min. After irradiation, each added solution was removed, and the cells were washed twice with culture medium (100 μL). A Cell Counting Kit-8 solution (100 μL, manufactured by DOJINDO LABORATORIES) was added to each well, and absorbance (wavelength 450 nm) was measured 2 hr later using a 96-well Microplate Reader (Labsystems Multiskan, trademark). The survival rate (%) of the corneal epithelial cell was determined using the following formula from the average value of absorbance of each test solution and the average value of absorbance of the non-treatment group.

$$\text{Survival rate (\%)} = \frac{\text{average value of absorbance of each test solution addition group}}{\text{average value of absorbance of non-treatment group}} \times 100$$

2. Experimental Results

As shown in Table 7, the survival rate of the corneal epithelial cell decreased by the irradiation of ultraviolet rays. However, the survival rate with the aqueous solution containing 0.4% xanthan gum showed a high value even after irradiation of ultraviolet rays. The results indicate that xanthan gum has a corneal epithelial cell protecting action against a disorder caused by ultraviolet rays.

TABLE 7

Corneal epithelial cell protecting action of xanthan
gum against disorder caused by ultraviolet rays

| | survival rate (%) of corneal epithelial cell | |
|---|---|---|
| | with ultraviolet irradiation | without ultraviolet irradiation |
| 0.4% xanthan gum aqueous solution | 85.8 | — |
| phosphate buffer | 39.4 | 78.1 |

Preparation Examples of the rye drops containing xanthan gum and an amino acid according to the present invention are shown in below.

Example 1

Artificial Lacrimal Fluid Containing Xanthan Gum and Sodium Chondroitin Sulfate

An artificial lacrimal fluid having the following formulation was prepared by a conventional method.

| sodium chondroitin sulfate | 0.5 g |
|---|---|
| sodium chloride | 0.5 g |
| boric acid | 0.3 g |
| sodium borate | e.q. |
| sodium citrate | 0.2 g |
| xanthan gum | 0.2 g |
| sorbic acid | 0.2 g |
| purified water | e.q. |
| total amount | 100 ml (pH 7.0) |

Example 2

Artificial Lacrimal Fluid Containing Xanthan Gum and Potassium L-Aspartate

An artificial lacrimal fluid having the following formulation was prepared by a conventional method.

| potassium L-aspartate | 1 g |
|---|---|
| sodium chloride | 0.5 g |
| boric acid | 0.2 g |
| sodium borate | e.q. |
| xanthan gum | 0.2 g |
| benzalkonium chloride solution (10 w/v %) (as benzalkonium chloride 0.005 g) | 0.05 ml |
| purified water | e.q. |
| total amount | 100 ml (pH 7.2) |

Example 3

Artificial Lacrimal Fluid Containing Xanthan Gum and Aminoethyl Sulfonic Acid

An artificial lacrimal fluid having the following formulation was prepared by a conventional method.

| | |
|---|---|
| aminoethyl sulfonic acid | 1 g |
| sodium chloride | 0.5 g |
| boric acid | 0.4 g |
| sodium borate | e.q. |
| xanthan gum | 0.1 g |
| benzalkonium chloride solution (10 w/v %) | 0.05 ml |
| (as benzalkonium chloride 0.005 g) | |
| purified water | e.q. |
| total amount | 100 ml (pH 7.2) |

Example 4

Eye Drops for Contact Lenses Containing Xanthan Gum and Sodium Chondroitin Sulfate Eye drops for contact lenses having the following formulation were prepared by a conventional method.

| | |
|---|---|
| sodium chondroitin sulfate | 0.5 g |
| sodium chloride | 0.55 g |
| potassium chloride | 0.15 g |
| boric acid | 0.5 g |
| sodium borate | e.q. |
| disodium edetate | 0.01 g |
| xanthan gum | 0.1 g |
| polysorbate 80 | 0.15 mL |
| chlorhexidine gluconate solution (20 w/v %) | 0.025 mL |
| (as chlorhexidine gluconate 0.005 g) | |
| purified water | e.q. |
| total amount | 100 ml (pH 7.2) |

Example 5

Contact Lens Solution Containing Xanthan Gum and Aminoethyl Sulfonic Acid

A contact lens solution having the following formulation was prepared by a conventional method.

| | |
|---|---|
| aminoethyl sulfonic acid | 1 g |
| partially hydrolyzed polyvinyl alcohol | 2 g |
| sodium chloride | 0.6 g |
| hydroxypropylmethylcellulose 2906 | 0.5 g |
| disodium edetate | 0.02 g |
| sodium acetate | 0.1 g |
| sodium hydroxide | e.q. |
| xanthan gum | 0.1 g |
| benzalkonium chloride solution (10 w/v %) | 0.05 mL |
| (as benzalkonium chloride 0.005 g) | |
| purified water | e.q. |
| total amount | 100 ml (pH 7.2) |

Example 6

Artificial Lacrimal Fluid Containing Xanthan Gum and Sodium Chondroitin Sulfate

An artificial lacrimal fluid having the following formulation was prepared by a conventional method.

| | |
|---|---|
| sodium chondroitin sulfate | 0.5 g |
| sodium chloride | 0.5 g |
| boric acid | 0.3 g |
| sodium borate | e.q. |
| sodium citrate | 0.2 g |
| xanthan gum | 0.3 g |
| sorbic acid | 0.2 g |
| purified water | e.q. |
| total amount | 100 ml (pH 7.0) |

Example 7

Artificial Lacrimal Fluid Containing Xanthan Gum and Potassium L-Aspartate

An artificial lacrimal fluid having the following formulation was prepared by a conventional method.

| | |
|---|---|
| potassium L-aspartate | 1 g |
| sodium chloride | 0.5 g |
| boric acid | 0.2 g |
| sodium borate | e.q. |
| xanthan gum | 0.4 g |
| benzalkonium chloride solution (10 w/v %) | 0.05 ml |
| (as benzalkonium chloride 0.005 g) | |
| purified water | e.q. |
| total amount | 100 ml (pH 7.2) |

Example 8

Artificial Lacrimal Fluid Containing Xanthan Gum and Aminoethyl Sulfonic Acid

An artificial lacrimal fluid having the following formulation was prepared by a conventional method.

| | |
|---|---|
| aminoethyl sulfonic acid | 1 g |
| sodium chloride | 0.5 g |
| boric acid | 0.4 g |
| sodium borate | e.q. |
| xanthan gum | 0.5 g |
| benzalkonium chloride solution (10 w/v %) | 0.05 ml |
| (as benzalkonium chloride 0.005 g) | |
| purified water | e.q. |
| total amount | 100 ml (pH 7.2) |

Example 9

Eye Drops for Contact Lenses Containing Xanthan Gum and Sodium Chondroitin Sulfate Eye drops for contact lens having the following formulation was prepared by a conventional method.

| | |
|---|---|
| sodium chondroitin sulfate | 0.5 g |
| sodium chloride | 0.55 g |
| potassium chloride | 0.15 g |
| boric acid | 0.5 g |
| sodium borate | e.q. |
| disodium edetate | 0.01 g |
| xanthan gum | 0.3 g |
| polysorbate80 | 0.15 mL |
| chlorhexidine gluconate solution (20 w/v %) (as chlorhexidine gluconate 0.005 g) | 0.025 mL |
| purified water | e.q. |
| total amount | 100 ml (pH 7.2) |

Example 10

Contact Lens Solution Containing Xanthan Gum and Potassium L-Aspartate

A contact lens solution having the following formulation was prepared by a conventional method.

| | |
|---|---|
| potassium L-aspartate | 1 g |
| partially hydrolyzed polyvinyl alcohol | 2 g |
| sodium chloride | 0.4 g |
| hydroxypropylmethylcellulose 2906 | 0.5 g |
| disodium edetate | 0.02 g |
| sodium acetate | 0.1 g |
| sodium hydroxide | e.q. |
| xanthan gum | 0.4 g |
| benzalkonium chloride solution (10 w/v %) (as benzalkonium chloride 0.005 g) | 0.05 mL |
| purified water | e.q. |
| total amount | 100 ml (pH 7.2) |

Example 11

Contact Lens Solution Containing Xanthan Gum and Aminoethyl Sulfonic Acid

A contact lens solution having the following formulation was prepared by a conventional method.

| | |
|---|---|
| aminoethyl sulfonic acid | 1 g |
| partially hydrolyzed polyvinyl alcohol | 2 g |
| sodium chloride | 0.6 g |
| hydroxypropylmethylcellulose 2906 | 0.5 g |
| disodium edetate | 0.02 g |
| sodium acetate | 0.1 g |
| sodium hydroxide | e.q. |
| xanthan gum | 0.5 g |
| benzalkonium chloride solution (10 w/v %) (as benzalkonium chloride 0.005 g) | 0.05 mL |
| purified water | e.q. |
| total amount | 100 ml (pH 7.2) |

INDUSTRIAL APPLICABILITY

According to the present invention, an ophthalmic composition containing xanthan gum, or xanthan gum and an amino acid, which has a superior corneal epithelial disorder-treating effect and a superior corneal epithelial cell protecting effect can be provided. The ophthalmic composition of the present invention is useful as an agent for the prophylaxis or treatment of lacrimal fluid decrease symptom, xerophthalmia, meibomian gland dysfunction, Sjogren's syndrome, keratoconjunctivitis sicca, blepharitis, Stevens-Johnson syndrome, dry eye syndrome such as dry eye and the like related to VDT operations, corneal and conjunctival epithelial disorder caused by dry eye and the like. In addition, the ophthalmic composition of the present invention is useful as an agent for the prophylaxis or treatment of corneal epithelial disorders caused by ultraviolet rays or corneal epithelial disorders caused by contact with a preservative.

Moreover, the ophthalmic composition of the present invention in the form of an eye drop has superior usability since it contains xanthan gum showing pseudoplasticity.

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

This application is based on application No. 2004-281588 filed in Japan, the contents of which are incorporated hereinto by reference.

The invention claimed is:

1. An ophthalmic composition comprising xanthan gum, and L-aspartate or a pharmacologically acceptable salt thereof, wherein the concentration of the xanthan gum is 0.05-0.4 w/v % and wherein the concentration of the L-aspartate or a pharmacologically acceptable salt thereof is 0.05-1 w/v %.

2. The ophthalmic composition of claim 1, which is an eye drop.

* * * * *